Figure 1:
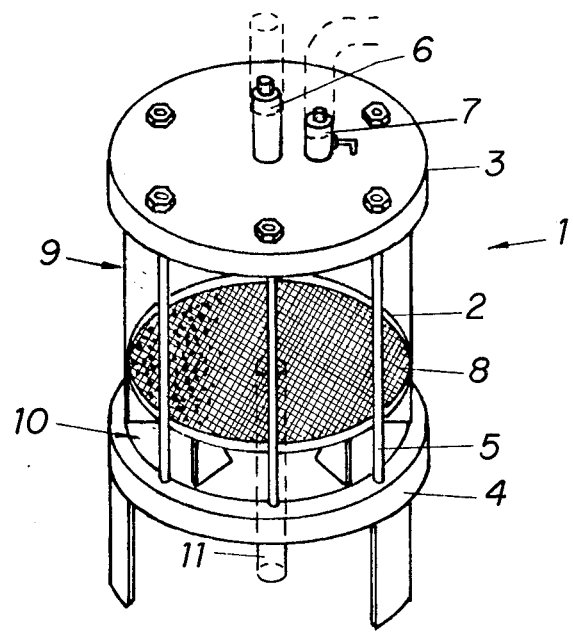

United States Patent [19]

Seufert

[11] 4,141,887
[45] Feb. 27, 1979

[54] PROCESS AND APPARATUS FOR THE PRODUCTION OF STERILE FILTERED BLOOD CLOTTING FACTORS

[76] Inventor: Arnold Seufert, Zehnstrasse 3, 8702 Hettstadt, Fed. Rep. of Germany

[21] Appl. No.: 800,776

[22] Filed: May 26, 1977

[30] Foreign Application Priority Data

May 31, 1976 [DE] Fed. Rep. of Germany ....... 2624373

[51] Int. Cl.² .......................... A23J 1/06; C07G 7/026
[52] U.S. Cl. .................................. 260/112 B; 210/71; 210/78; 210/DIG. 23
[58] Field of Search ..................... 210/65, 71, 72, 78, 210/77, 175, 252, 257 R, 257 M, 258, 321 R, 321 A, 321 B, 416 R, 416 M, 433 M, 500 M, DIG. 23; 424/11, 101, 177; 23/230 B, 259, 292; 128/214 R, 272; 260/112 B, 112.5 R

[56] References Cited

U.S. PATENT DOCUMENTS

| | | | |
|---|---|---|---|
| 2,521,121 | 9/1950 | Kilpatrick | 210/258 |
| 2,543,808 | 3/1951 | Seegers et al. | 424/177 |
| 2,864,506 | 12/1958 | Hiskey | 210/DIG. 23 |
| 3,005,556 | 10/1961 | Jensen | 210/488 |
| 3,145,713 | 8/1964 | Latham | 128/214 R |
| 3,449,314 | 6/1969 | Pollack | 424/11 |
| 3,560,377 | 2/1971 | Loeffler | 210/DIG. 23 |
| 3,631,018 | 12/1971 | Shanbrom et al. | 424/177 |
| 3,717,708 | 2/1973 | Wada et al. | 260/112 B |
| 3,803,115 | 4/1974 | Fekete et al. | 424/177 |
| 4,022,758 | 5/1977 | Andersson et al. | 260/112 B |
| 4,025,618 | 5/1977 | Garber et al. | 424/101 |

*Primary Examiner*—Frank Sever
*Attorney, Agent, or Firm*—Allison C. Collard; Thomas M. Galgano

[57] ABSTRACT

A process for the manufacture of sterile filtered blood-clotting products includes the steps of extracting blood from at least one donor, physically separating the blood to obtain substantially purified plasma free of cellular components, deep freezing the purified plasma at a temperature below about minus 22° C. to preserve Factor VIII, thawing the plasma to produce a cryo-precipitate, enriching the cryo-precipitate by physical treatment and physically separating the cryo-precipitate from the thawed plasma. The cryo-precipitate is then dissolved in a buffer and is sterile filtered by means of a static filtration with an autoclaved filtration device at a pressure difference of less than 0.5 atm. An apparatus for carrying out the process is also provided.

9 Claims, 5 Drawing Figures

PROCESS AND APPARATUS FOR THE PRODUCTION OF STERILE FILTERED BLOOD CLOTTING FACTORS

The invention concerns a process and an apparatus for the production of sterile filtered blood clotting factors, particularly from cryo-precipitate and/or fibrinogen with an enrichment of the Factors VIII and/or I.

During blood coagulation, a complicated enzymatic process converts the liquid blood into blood clots, which brings about sealing of the damaged blood vessel by the formation of a scab. Clotting difficulties are caused by the fact that some substances necessary for clotting are lacking in the blood, or that substances which prevent clotting are present to a greater degree. Clotting difficulties can be sucessfully treated by transfusions of blood clotting products, such as e.g. cryoprecipitate and fibrinogen with a concentrated Factor VIII or Factor I content.

The preparation of these blood clotting products can be carried out in a known way by means of the processes described below.

According to one of the first processes, several blood donations are taken from donors, and mixed to form a pool. The precipitation of the solid components of the blood, namely leucocytes, thrombocytes and erythrocytes, to give a plasma for further processing, is carried out by deposition or by centrifuging the pool. Finally, the relatively pure plasma is deep-frozen in minutes to minus 40° C. and stored at this temperature until analytical results have been obtained. After thawing the deep-frozen plasma to plus 2° to 4° C., cold centrifuging is carried out at these temperatures, which precipitates a cold precipitate (cryo-precipitate) with a higher concentration of Factor VIII. After dissolving the cryo-precipitate in a buffer, the solution is deep-frozen in special plants and stored at about minus 40° C. When required, several of these small products can be put together and after thawing be administered to patients with inherited or acquired clotting difficulties.

Another process depends on the fact that cryoprecipitate dissolved in a buffer is additionally freeze-dried (lyophilised) after deep-freezing. This lyophilised cryo-precipitate can be stored in commercial refrigerators at 2° to 8° C., and is readily available when required. The cryo-precipitate is enriched with respect to the Factors I, V, VIII and XIII, of which the very labile Factor VIII is of the greatest importance. When needed, the lyophilised cryo-precipitate can be redissolved in water which has been warmed to 20° to 30° C., and is then available within 5 to 10 minutes.

While the two processes described above for the production of blood clotting products are mainly used for blood donor purposes, there is another process used by industry in which the plasma taken for the preparation of cryo-precipitate is made from a pool of about 45 to 20,000 blood donations. The plasma is, here too, subjected to a cold treatment, centrifuged after thawing and the cryo-precipitate thus obtained in larger quantities, dissolved in a special buffer and subjected to a final sterile filtration in a suitable plant which is relatively large and expensive. The sterile filtered product can then be deep-frozen and freeze dried when, as already stated, it can be stored at plus 2° to plus 8° C.

Finally, a fourth process for the preparation of cryo-precipitate with concentrated Factor VIII content has been described, in which the plasma which has been deep-frozen at minus 40° C., is centrifuged in an centrifuge at plus 20° C. for 90 minutes. During this centrifuging stage, the contents of the bag of flask are warmed to about 4° C. while the cryo-precipitate deposited by the cooling immediately centrifuges out to the bottom. The methods already described for the other processes regarding the storage of the cryo-precipitate obtained, also apply here.

The above methods have the following main disadvantages, which calls into question their introduction on the grounds of efficiency, medical considerations and reasons connected with the difficulty of carrying them out.

For the first two processes, a blood plasma is used which is relatively impure in leucocytes and thrombocytes, so that later sterile filtration of the cryo-precipitate obtained can lead to considerable difficulties since the filter may become prematurely blocked. The filtration does not give a therapeutically useful product with the filtration techniques at present in use.

A further disadvantage of the first process is that great technical expenditure is necessary for the freezing and storage, which cannot be met by a hospital or for patients with haemophilia A, and the product can only be transfused when needed after a longer preparation time so that it cannot be used in cases of emergency. While this disadvantage is not present with the lyophilised cryo-precipitate made by the second process, i.e. the technical expenditure required is small, the blood clotting product obtained by the second process, like that obtained by the first process, has the disadvantage that the products are not subject to sterile filtration and contain components which are not dissolved with molecular dispersion (clear solution), but are partially dissolved with colloidal dispersion (alum-like). Larger colloidally-dispersed particles are deposited in the capillaries and this leads to an increased danger of microembolism. With colloidally-dispersed solutions, the endpoint of the dissolution process is difficult to determine because of the opacity of the product. In practice, a great deal of time is usually lost in hospitals before the dissolved product can be transfused. The doctor dealing with an emergency needs clotting products which can be rapidly transfused. In addition, it cannot be ascertained with certainty whether the product is sterile or not so that the danger of bacterial infection or sepsis on transfusion is increased.

Furthermore, the products produced by the two previous processes have no definite Factor VIII content.

The third process, or industrially-used process described for the production of cryo-precipitate from large pools, does, however, possess all the advantages of sterile filtration but with these products there is a significantly increased danger of infection by virus hepatites by transfusion of infected material (Hepatitis B).

It is a valid statement, that the danger of hepatitis from blood clotting products is as great as that for whole blood in corresponding amount. E.g. the cryo-precipitate made from 45 individual donations, carries a hepatitis risk the same as 45 individual blood transfusions together. The hepatitis risk therefore increases with the size of the pool from which it is obtained.

The disadvantage of the fourth previously described process is that a cryo-precipitate with a very high protein content is centrifuged out, and this leads to a subsequent sterile filtration which involves blocking of the filter in the shortest possible time. Therapeutically valuable sterile filtered products are therefore not obtainable using this process.

The invention is therefore basically aimed at the problem of creating a process and an apparatus of the above-mentioned type, which makes it possible to obtain a loss-free efficient preparation of sterile, filtered, clear soluble blood-clotting products, with a high concentration of Factor VIII or I, or a combination of these Factors, with a minimal rate for hepatitis, and so that the products are rapidly and readily available as a result of lyophilisation.

The process according to the invention, is characterised by the fact that at least one blood extraction, which has come from a minimum number of donors, preferably one donor, is physically separated to produce plasma, until the plasma is almost absolutely purified of cellular components, the highly purified plasma is deep frozen at a lower temperature than the temperature of about minus 22° C. which is critical for the preservation of Factor VIII, and is finally thawed again, preferably to about plus 2° C., the cold precipitate (cryo-precipitate) from the thawed plasma is enriched at this temperature by physical treatment, preferably centrifuging, and separated from the residual plasma, the concentrated cryo-precipitate is dissolved in a buffer and then filtered under sterile conditions by means of a static filtration using an autoclaved filtration apparatus, at a pressure difference of <0.5 atm.

By using a single blood donation as starting material for obtaining the plasma, the risk of virus-hepatitis infection on transfusion of the cryo-precipitate obtained, is reduced to about 0.3% per single blood donation, while this risk for obtaining cryo-precipitate from large pools in the normal way, is approximately 14% according to data given in the technical literature.

By physically separating the plasma from the solid components of the blood, which is preferably carried out in two sequential centrifugation stages in the process according to the invention, a highly-purified plasma is obtained in an advantageous manner, in which almost all the solid particles of the blood are removed. The filter cannot become prematurely blocked, so that the whole of the concentrate volume passes through the filter without loss.

Another advantageous characteristic of the process according to the invention, is that the thawing process which follows deep-freezing, is accelerated by the addition of heat by means of a thermostated or thermostat-controlled liquid bath, and that the final temperature of the plasma supplied for cold centrifuging, is about 2° C. With a higher thaw temperature and a slower thawing process, more Factor VIII in particular may go into solution from the cryo-precipitate and no longer be centrifuged out. It also prevents the tendency of the precipitate to entrain dissolved proteins, and thus the protein concentration in the precipitate is relatively small for the same Factor VIII content. The low protein content is necessary for the prevention of a premature blocking of the filter.

After centrifuging, as another advantageous characteristic of the invention, the plasma present in the cryo-precipitate layer is almost completely sucked off and used for the preparation of fibrinogen (Cohn-I fraction). The cryo-precipitate obtained is dissolved in a buffer, e.g. in sodium chloride and/or sodium citrate and subjected to sterile filtration. This sterile filtration occurs, in an advantageous manner, in a sterile chamber (laminar-flow-box) will prevention of secondary contaminations. During the static filtration, a constant pressure of <0.5 atm is used to advantage, since otherwise the danger of gel polarization may occur during the static filtration. This is caused by the fact that during static filtration the direction o flow of the solvent and the direction of the pressure is the same, so that the solvent passes rapidly through the pores of the filter and the fibrinogens in the hydrate envelopes deposit as a gel layer in front of the filter and block it.

This disadvantage is prevented by the so-called over-current technique, in which the direction of flow of the solvent is at right angles to the pressure direction, and the fibrinogens deposited on the filter pores are broken up and a reduction in the concentration polarization of the particles is facilitated, but this process is not suitable for the sterile filtration of cryo-precipitates obtained from single blood donations because of the high technical expense.

After the loss-free preparation of cryoprecipitate according to the invention, as described above, the blood clotting products after sterile filtration are deep frozen and lyophilised.

In order to check on the fact that the sterile filtration has proceeded without error, after each process the so-called bubble-point-test is carried out to advantage, i.e. the filtration apparatus is subjected to a pressure, in $kg/cm^2$, which is necessary to force the pressurising gas through the filter wetted with water. If gas bubbles appear on the sterile filtered side of the filter at a pressure below that of the predetermined pressure, it is an indication that the filter has been damaged during the experiment or before the experiment.

According to the process, in addition, purification and autoclaving of the filtration apparatus with a newly-inserted filter combination is carried out before any subsequent sterile filtration. In this way any remaining hepatitis viruses or previously processed blood is prevented from being carried over into the next batch of blood to be processed.

The apparatus provided for carrying out the process according to the invention, is characterised by the fact that a closed pressure vessel is used for the sterile filtration, which serves as a receiver for the blood clotting products to be subjected to sterile filtration, and which is divided into two chambers by at least one filter layer, one of the chambers having a connection for the introduction of inert pressurising gas, while the other chamber is connected to a discharge connection. The pressure vessel is preferably of such dimensions as necessary for it to be able to accept the amount of concentrate necessary for the preparation of an effective dose of cryo-precipitate. Preferably, the pressure vessel is a polycarbonate cylinder or a stainless steel cylinder, which is clamped between two pressure flanges, these closing the pressure vessel on the front side, and which have the appropriate connections. The apparatus can be autoclaved in preparation for the manufacture of a blood clotting product from at least one blood donation, so that the transfer of any residual bacteria or viruses is prevented. The autoclaving can be carried out in the normal way in an autoclave.

According to a further advantageous characteristic of the invention, the pressure vessel is divided into two chambers by a filter layer which consists of serveral filters, so that the filter used for the unfiltered product always has a greater pore size than the next filter. Membrane filters can be used advantageously as filters, the smallest pore size being, preferably 0.22 μm. Since the individual filters are very thin, suitable spacing devices or supporting fittings can be placed between them.

As already mentioned, care must be taken with membrane filters of this size, to ensure that during static sterile filtration methods gel polarization is prevented, since it may lead to blocking of the filter prematurely. Filters of the above-named size can be used in the process according to the invention, because a highly purified plasma is to be processed, which is almost absolutely free from cellular components, because the cryo-precipitate centrifuged out in the cold centrifuge has a maximum protein concentration and because operation is carried out with a pressure of <0.5 atm. so that the above-described concentration polarization does not occur. The whole of the cryo-precipitate concentrate placed in the pressure vessel is therefore filtered sterile without loss.

For the continuous preparation of sterile filtered blood clotting products it is possible, according to another advantageous characteristic of the invention, to connect several pressure vessels in parallel and have them joined to a common pressure source, in particular a source of inert gas. Between the inert gas source and the respective pressure vessels a pressure control and a pressure measuring apparatus can be included. The maximum inert gas pressure for the gas source is preferably above the bubble-point pressure of the filter with the smallest pore size, so that the pressure control adjusts the pressure for carrying out the sterile filtration to <0.5 atm, while for carrying out the bubble-point test after completion of the sterile filtration, it is adjusted to the bubble-point pressure selected for the corresponding filter, which e.g. is 3.8 atm. for the above-mentioned filter with pore size 0.22 μm.

The parallel pressure vessels are preferably arranged in a laminar-flow box, so that secondary contamination is prevented.

The removal connection on the pressure vessel is preferably connected to a detachable sterile receiver vessel. In this way it is possible to remove continuously from the sterile filtration plant, blood clotting products which can be used for a transfusion or for lyophilisation.

Figure 2:
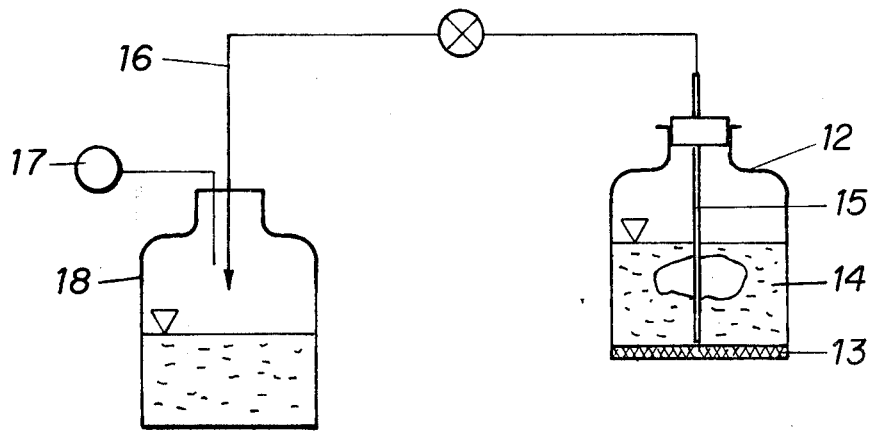
Figure 3:
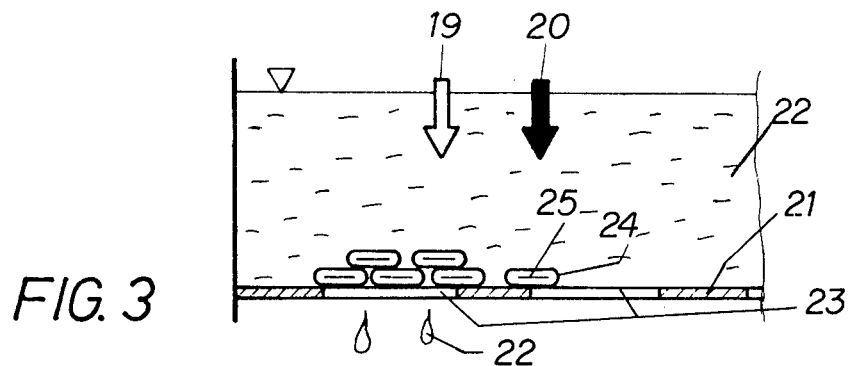
Figure 4:
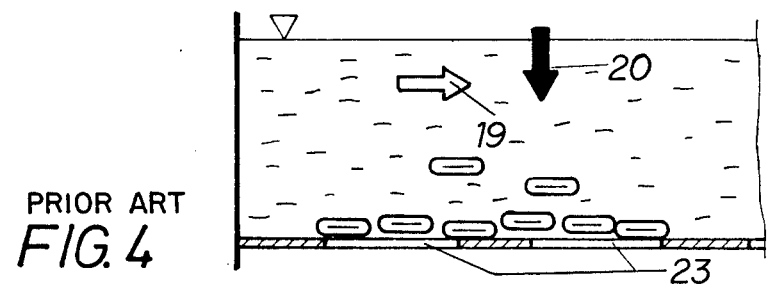
Figure 5:
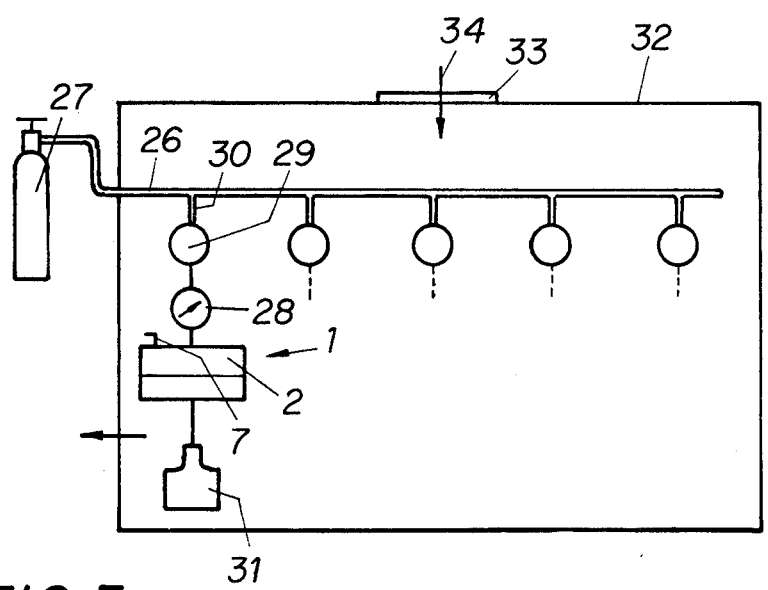

Other characteristics and advantages of the invention are indicated in the following description of a design example by means of the diagramms. These show, as follows:

FIG. 1 a diagrammatic view of the sterile filtration apparatus for carrying out the process according to the invention;

FIG. 2 a diagrammatic representation of equipment which is used for obtaining a concentrated cryo-precipitate with a minimum protein content and for separating the residual plasma;

FIG. 3 a very diagrammatic representation of gel polarisation during a static filtration process;

FIG. 4 a very diagrammatic representation of gel polarization using the over current technique and FIG. 5 a diagrammatic representation of a unit of devices connected in parallel for the continuous preparation of sterile filtered blood clotting products.

The filtration apparatus 1, shown diagrammatically in FIG. 1, which is used for the static sterile filtration of cryo-precipitate concentrates, is built up from several parts, and consists primarily of a pressure vessel 2, which is closed on both its front sides with covers 3 and 4, which are held against the pressure vessel by means of tension screws or other suitable means, 5. The pressure vessel can be transparent so that the filtration process can be observed.

Inert gas, in particular nitrogen, may be introduced into the pressure vessel 2 through the connection 6 provided on the upper cover, while the cryo-precipitate with a small protein content and a high Factor VIII concentration centrifuged out by cold centrifuging, is introduces into the pressure vessel through the connection 7.

The internal space of the pressure vessel 2, is divided into an upper and a lower chamber, 9 and 10, by a filter layer 8, the upper chamber being connected to the two connections 6 and 7, while the lower chamber 10, is connected to a discharge connection 11.

The filter layer 8, consists of several filters, which can be held apart by spacers, the individual filters being arranged so that the filter facing the direction of chamber 9 has the largest pore size, while the filter adjacent to the lower chamber 10, has the smallest pore size, preferably 0.22 μm. Membrane filters are used as filters.

In FIG. 2 are shown, diagrammatically, two containers, namely a container 12 in which there is the cryo-precipitate 13, centrifuged out during cold centrifuging, and the residual plasma 14, which is directly sucked out from above the cryo-precipitate layer by means of a hollow needle 15, a flexible tube 16 to a low pressure source 17, or a suction pump connected to the flexible tube 16, and then collected in the container 18. The plasma in the collection container, is used again for the preparation of fibrinogen.

The cryo-precipitate collected in the container 12 has, according to the invention, a high Factor VIII concentration, a very low protein concentration and virtually no blood particles.

In the static filtration process shown very diagrammatically in FIG. 3, the direction of flow, indicated by the arrow 19, and the pressure direction, indicated by the arrow 20, are the same at right angles to the filter 21. If too high a pressure is selected for the static sterile filtration, then the solvent, 22, passes too rapidly through the pores 23, so that fibrinogen 25, enclosed in a hydrate envelope 24, is deposited as a layer on the filter. The filter is thus blocked up in a very short time, so that not all the quantity of cryo-precipitate dissolved in the buffer, is sterile filtered and consequently the loss in efficiency is considerable.

In order to achieve the projected loss-free sterile filtration, it is necessary to prevent gel polarisation by using a low pressure differential, to use a highly purified blood plasma and to prepare the cryo-precipitate concentrate with a minimum protein content.

FIG. 4 shows the well-known overcurrent technique, which cannot be used for the process according to the invention because of the high technical expense. With this technique, the direction of flow 19, is at right angles to the pressure direction 20, so that the fibrinogens do not collect so quickly on the pores 23 of filter 21 and block them up.

Finally, FIG. 5 shows a unit of pieces of apparatus 1, connected in parallel, of which only one apparatus is shown diagrammatically for simplicity. The individual pieces of apparatus are connected to a pressure gas header tube 26, which is connected to a source of inert gas 27. Each filtration apparatus 1, is connected to the pressure gas header tube 26 by means of a manometer 28 and a pressure control 29 on a branch line 30.

In order to carry out the sterile filtration with the filtration apparatus 1, which has been previously autoclaved with the filter layer 8 already inserted, the cryo-precipitate dissolved in buffer is introduced into the pressure vessel 2, through the connection 7. Then a pressure of less than 0.5 atm is applied by means of the pressure control 29, and the filtration begins. Of course, the filtration process can be carried out with the filtration apparatus beside one another, or in sequence, so that the sterile filtered blood clotting products collected in the sterile receiver 31 can be removed continuously.

After completion of a filtration process, the so-called bubble-point test is carried out, in which the bubble-point pressure predetermined for the filter used is set. It is necessary that the maximum pressure of the inert gas source 27, is greater than the bubble-point pressure.

The filtration apparatus connected in parallel, are in a laminar flow box 32, i.e. in a sterile chamber, into which purified air flows from outside through the sterile filter 33, in the direction of arrow 34.

I claim:

1. A process for the manufacture of sterile filtered blood-clotting products concentrated in Factor VIII comprising the steps of:
    extracting blood from a number of at least one donor; said number being sufficiently low to reduce the risk of virus-hepatitus infection to about 0.3%;
    physically separating the blood to obtain substantially purified plasma, free of cellular components, said separating step being carried out in a sequence of at least two centrifuging steps, to obtain plasma with an increasing degree of purity;
    deep freezing the purified plasma at a temperature below about minus 22° C., to preserve Factor VIII;
    thawing the plasma to produce a cryo-precipitate;
    enriching and physically separating the cryo-precipitate from the thawed plasma by centrifuging;
    dissolve the cryo-precipitate in a buffer; and
    effecting a sterile filtration of the buffer-dissolved, cryo-precipitate by means of a static filtration device at a pressure of less than 0.5 atm.

2. The process according to claim 1, wherein said blood is extracted from only one donor.

3. The process according to claim 1, wherein said thawing and enriching steps are carried out at a temperature of about plus 2° C.

4. The process according to claim 1, wherein said thawing step is accelerated by the input of heat by means of a thermostat-controlled liquid bath.

5. The process according to claim 1 additionally including the step of drawing off substantially all of the plasma present above the cryo-precipitate layer, so that it may be used for obtaining fibrinogen.

6. The process according to claim 1 wherein said sterile filtration step is carried out in a sterile chamber to prevent secondary contamination.

7. The process according to claim 1 additionally including the step of carrying out a bubble-point test after said sterile filtration step, to ensure that the process has proceeded without error.

8. The process according to claim 1, wherein said process steps are repeated following purification and autoclaving of the filtration apparatus employed.

9. The process according to claim 1 additionally including the step of deep freezing and freeze drying the sterile filtered cryo-precipitate obtained from the blood extraction.

10. The process according to claim 1, wherein said sterile filtration step is effected by filtering said buffer-dissolved, cryo-precipitate in a static filtration device through a plurality of space-apart, superimposed filters of decreasing pore sizes, the uppermost filter having the largest pore size and the lowermost filter having the smallest pore size.

* * * * *

UNITED STATES PATENT OFFICE
CERTIFICATE OF CORRECTION

Patent No. 4,141,887          Dated Feb. 27, 1979

Inventor(s) Arnold Seufert

It is certified that error appears in the above-identified patent and that said Letters Patent are hereby corrected as shown below:

> Column 3, line 68, delete "will" and substitute therefor --with--. Column 4, line 5, delete "o" and substitute therefor --of--. Column 5, line 12, delete "maximum" and substitute therefor --minimum--. Claim 10, line 4, delete "space-apart" and substitute therefor --spaced apart--.

Signed and Sealed this

Twenty-first Day of August 1979

[SEAL]

*Attest:*

*Attesting Officer*
         LUTRELLE F. PARKER
         *Acting Commissioner of Patents and Trademarks*